(12) United States Patent
Dalko et al.

(10) Patent No.: US 7,622,448 B2
(45) Date of Patent: Nov. 24, 2009

(54) COMPOSITIONS SUITABLE FOR TOPICAL APPLICATION TO THE SKIN

(75) Inventors: Maria Dalko, Gif S/Yvette (FR);
Alexandre Cavezza, Tremblay-En-France (FR); Dominique Bernard, Paris (FR)

(73) Assignee: L'Oreal, Paris (FR)

( * ) Notice: Subject to any disclaimer, the term of this patent is extended or adjusted under 35 U.S.C. 154(b) by 253 days.

(21) Appl. No.: 10/813,056

(22) Filed: Mar. 31, 2004

(65) Prior Publication Data

US 2005/0002889 A1 Jan. 6, 2005

Related U.S. Application Data

(60) Provisional application No. 60/471,725, filed on May 20, 2003.

(30) Foreign Application Priority Data

Apr. 8, 2003 (FR) ................... 03 04349

(51) Int. Cl.
*A61K 31/70* (2006.01)
*A01N 43/04* (2006.01)
*A61K 31/715* (2006.01)
(52) U.S. Cl. ...................................... 514/23
(58) Field of Classification Search ............... None
See application file for complete search history.

(56) References Cited

U.S. PATENT DOCUMENTS

| | | | |
|---|---|---|---|
| 4,299,845 | A | 11/1981 | Loebenberg et al. |
| 5,175,340 | A | 12/1992 | Forestier et al. |
| 5,412,120 | A | 5/1995 | Fischer et al. |
| 5,653,970 | A | 8/1997 | Vermeer |
| 2004/0048785 | A1 | 3/2004 | Dalko et al. |

| | | | |
|---|---|---|---|
| 2004/0198977 | A1 | 10/2004 | Richard et al. |

FOREIGN PATENT DOCUMENTS

| | | |
|---|---|---|
| EP | 0 350 386 | 1/1990 |
| FR | 2 852 009 | 9/2004 |
| JP | 2-59541 | 2/1990 |
| JP | 5-271153 | 10/1993 |
| JP | 2000-344614 | 12/2000 |
| JP | 2001-172274 | 6/2001 |
| JP | 2004-525877 | 8/2004 |

(Continued)

OTHER PUBLICATIONS

Son, et al. "Free Radical Scavenging and Antioxidative Activity of Caffeic Acid Amide and Ester Analogues: Structure-Activity Relationship." Journal of Agricultural and Food Chemistry 2002, 50, 468-472.*

(Continued)

*Primary Examiner*—Shaojia Anna Jiang
*Assistant Examiner*—Layla Bland
(74) *Attorney, Agent, or Firm*—Oblon, Spivak, McClelland, Maier & Neustadt, L.L.P.

(57) ABSTRACT

The present invention relates to compositions that are suitable for topical application to the skin or the scalp, containing, in a physiologically acceptable medium, at least one compound of a given formula. The invention also relates to a cosmetic treatment process comprising the topical application of these compositions and also to novel C-glycoside derivatives.

17 Claims, 1 Drawing Sheet

FOREIGN PATENT DOCUMENTS

JP      2004-262943      9/2004

OTHER PUBLICATIONS

Kametani, et al. "New Entry to the C-Glycosilation by means of Carbenoid Displacement Reaction. Its Application to the Synthesis of Showdomycin." Journal of the American Chemical Society 1987, 109, 3010-3017.*

Bates et al. J. Org. Chem. 1983, 48, 4479-4481.*

L Anderson et al. "Carbohydrate Rearch," vol. 257, No. 1, (1994) p. 81-95.

Guenter Wulff et al.; "On the synthesis of C-glycosyl compounds containing double bonds without the use of protecting groups"; Carbohydrate Research, vol. 257, 1994; pp. 81-95.

* cited by examiner

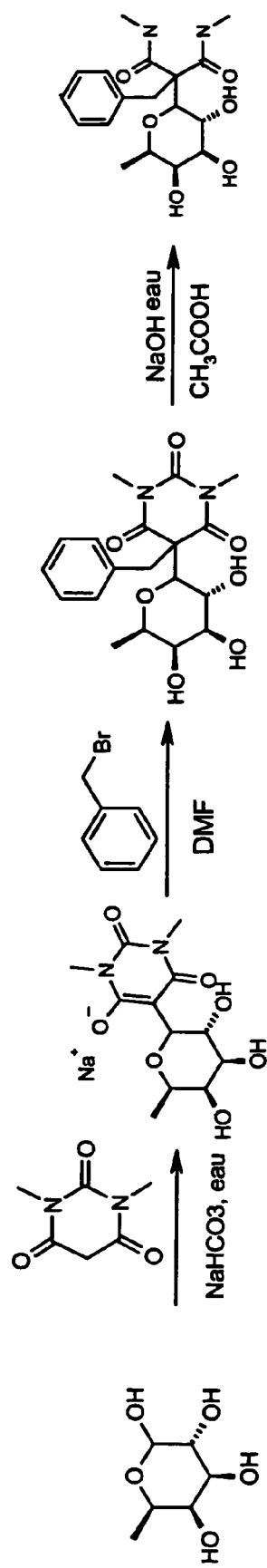
FIGURE UNIQUE

COMPOSITIONS SUITABLE FOR TOPICAL APPLICATION TO THE SKIN

REFERENCE TO PRIOR APPLICATIONS

This application claims priority to U.S. provisional application No. 60/471,725 filed May 20, 2003, and to French patent application 0304349 filed Apr. 8, 2003, both incorporated herein by reference.

FIELD OF THE INVENTION

The present invention relates to compositions that are suitable for topical application to the skin or the scalp, containing, in a physiologically acceptable medium, at least one compound of a given formula. The invention also relates to a cosmetic treatment process comprising the topical application of these compositions and also of novel C-glycoside derivatives.

In a preferred embodiment the invention relates to a composition that is suitable for topical application to the skin or the scalp, comprising, in a physiologically acceptable medium, at least one compound of formula (I)

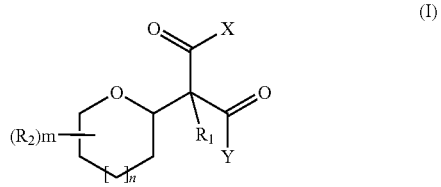

The invention also relates in a preferred embodiment to a cosmetic treatment process comprising the topical application to the skin of this composition, in particular in order to prevent or fade out the signs of ageing of the skin and/or to improve the radiance of the complexion and/or to combat dry skin.

The invention also relates in a preferred embodiment to novel C-glycoside derivatives (III):

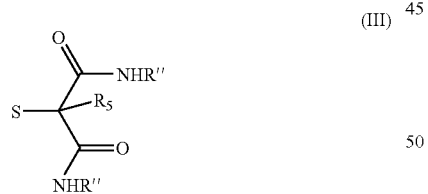

in which S is a monosaccharide or a polysaccharide.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Human skin consists of two compartments, namely a surface compartment, the epidermis, and a deep compartment, the dermis.

Natural human epidermis is composed mainly of three types of cells: the keratinocytes, which form the vast majority, the melanocytes and the Langerhans cells. Each of these cell types contributes via its intrinsic functions to the essential role played by the skin in the body.

During the process known as keratinization, the keratinocytes located in the basal layer of the epidermis multiply and grow, thus pushing the older epidermal cells upwards and towards the surface of the epidermis. During this displacement, these cells become flattened and differentiate to form keratin. The dead surface cells resulting from this keratinization process (corneocytes) constitute the horny layer of the epidermis, where they are separated by lipid layers and linked together via protein linkages (corneosomes). These dead cells are gradually removed from the surface of the skin and replaced with new keratinized cells.

In young, healthy skin, the desquamation of the skin that takes place in this way is characterized by the removal of individual cells or of small lumps of cells. In contrast, with age or in the case of certain pathologies, desquamation may be impaired, in the sense that an excess of keratin material is formed at the surface of the skin, resulting either in a removal of the stratum corneum in the form of squamae (ageing of the skin or dry skin), or in an obstruction of the sebaceous follicles (acne).

The use of desquamating agents, such as $\alpha$-hydroxy acids and $\beta$-hydroxy acids (in particular salicylic acid), is thus generally indicated in the cosmetic or dermatological treatment of the abovementioned skin disorders.

It nevertheless remains that the desire to maintain a youthful appearance and/or healthy skin continues to lead to the incessant search for novel compounds and/or novel compositions for maintaining or improving the appearance of the skin.

SUMMARY OF THE INVENTION

The inventors have now discovered, surprisingly and unexpectedly, that certain compounds, in particular C-glycoside derivatives, have desquamating properties that allow them to be used in the prevention or treatment of the signs of ageing of the skin, dry skin and acne, etc.

BRIEF DESCRIPTION OF THE DRAWINGS

FIG. 1 illustrates a process for preparing 2-benzyl-N,N'-dimethyl-2-(3,4,5-trihydroxy-6-methyltetrahydropyran-2-yl)malonamide in three steps.

DETAILED DESCRIPTION OF THE PREFERRED EMBODIMENTS

One subject of the present invention is a composition that is suitable for topical application to the skin or the scalp, comprising, in a physiologically acceptable medium, at least one compound corresponding to formula (I):

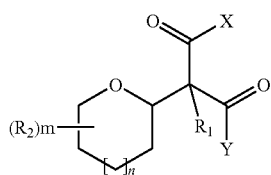

(I)

in which:

$R_1$ represents a hydrogen atom or a group chosen from:
- a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle, in which R and R' represent, independently of each other, a hydrogen atom or a saturated or unsaturated, linear, cyclic or branched $C_1$-$C_{12}$ alkyl group,
- a halogen atom, for example a fluorine, chlorine, bromine or iodine atom,
- an aryl group optionally substituted with one or more groups chosen from: —OR, —SR, —COOR, —NRR', halogen, sulphate and phosphate, in which R and R' have the meaning given above;

$R_2$ represents a group chosen from:
- $R_{21}$ in which $R_{21}$ has the definition given above for $R_1$,
- $OR_{22}$, in which $R_{22}$ has the definition given above for $R_1$, with the exception of halogen,
- $OR_{23}$, in which $R_{23}$ is a sulphate, phosphate, glycoside or alkylcarbonyl group, or a heterocycle,
- $NR_{24}R_{25}$, in which $R_{24}$ and $R_{25}$ independently represent a group having one of the definitions given above for $R_1$, with the exception of halogen,
- $NR_{26}R_{27}$, in which $R_{26}$ and $R_{27}$ independently represent a glycoside or alkylcarbonyl radical or a heterocycle,
- a sulphate or phosphate group;

X and Y represent, independently of each other, a radical —$OR_3$ or —$NR_3R_4$, in which $R_3$ and $R_4$ are independently chosen from:
- a hydrogen atom,
- a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle, in which R and R' have the meaning given above,
- an aryl group optionally substituted with one or more groups chosen from: —OR, —SR, —COOR, —NRR', halogen, sulphate and phosphate, in which R and R' have the meaning given above,
- or $R_3$ and $R_4$ together form a ring containing from 5 to 7 atoms with the nitrogen atom to which they are attached, or X and Y form a ring of 6 or 7 carbon atoms with the three carbon atoms separating them;

n is an integer equal to 0 or 1; and m is an integer equal to 0, 1, 2, 3 or 4.

According to one preferred embodiment of the invention, $R_2$ represents a group chosen from:
- a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle, in which R and R' represent, independently of each other, a hydrogen atom or a saturated or unsaturated, linear, cyclic or branched $C_1$-$C_{12}$ alkyl group,
- $OR_{22}$, in which $R_{22}$ is a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle, in which R and R' represent, independently of each other, a hydrogen atom or a saturated or unsaturated, linear, cyclic or branched $C_1$-$C_{12}$ alkyl group,
- $OR_{23}$, in which $R_{23}$ is a sulphate, phosphate or glycoside group, or a heterocycle,
- $NR_{24}R_{25}$, in which $R_{24}$ and $R_{25}$ independently represent a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle, in which R and R' represent, independently of each other, a hydrogen atom or a saturated or unsaturated, linear, cyclic or branched $C_1$-$C_{12}$ alkyl group,
- $NR_{26}R_{27}$, in which $R_{26}$ and $R_{27}$ independently represent a glycoside or alkylcarbonyl radical or a heterocycle,
- a sulphate or phosphate group.

Advantageously, X and Y represent, independently of each other, a radical —OH or —$NR_3R_4$, in which $R_3$ and $R_4$ are independently chosen from:
- a hydrogen atom,
- a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle,
- an aryl group optionally substituted with one or more groups chosen from: —OR, —SR, —COOR, —NRR', halogen, sulphate and phosphate, in which R and R' represent, independently of each other, a hydrogen atom or a saturated or unsaturated, linear, cyclic or branched $C_1$-$C_{12}$ alkyl group,
- or $R_3$ and $R_4$ together form a ring containing from 5 to 7 atoms with the nitrogen atom to which they are attached, or X and Y form a ring of 6 or 7 carbon atoms with the three carbon atoms separating them.

According to one particularly preferred embodiment of the invention, in formula (I) above, at least one of the following conditions is satisfied:
- $R_1$ is a fluorine or hydrogen atom or an unsubstituted alkyl or benzyl radical,
- $R_2$ is a hydroxyl, hydroxyalkyl or alkyl group or a sugar residue,
- X and Y are groups —$NR_3R_4$ in which $R_3$ and $R_4$ are chosen independently from a hydrogen atom and a methyl, ethyl, n-propyl or isopropyl radical, and
- n is equal to 1.

According to one particularly preferred embodiment of the invention, the compound of formula (I) is a C-glycoside derivative corresponding to formula (II) below:

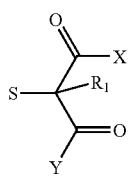

(II)

in which:
S represents a monosaccharide or a polysaccharide containing up to 20 sugar units, in pyranose and/or furanose form and of L and/or D series, the said monosaccharide or polysaccharide containing at least one free hydroxyl function,
the S—C bond represents a bond of C-anomeric nature,
$R_1$, X and Y have the meaning given above.

Advantageously, the preferred monosaccharides are chosen from D-glucose, D-galactose, D-mannose, D-xylose, D-lyxose, L-fucose, L-arabinose, L-rhamnose, D-glucuronic acid, D-galacturonic acid, D-iduronic acid, N-acetyl-D-glucosamine and N-acetyl-D-galactosamine.

Advantageously also, the preferred polysaccharides contain up to 6 sugar units and are chosen especially from D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine, N-acetyl-D-glucosamine, an oligosaccharide containing at least one xylose advantageously chosen from xylobiose, methyl-β-xylobioside, xylotriose, xylotetrose, xylopentose and xylohexose and preferably xylobiose, which is composed of two xylose molecules linked via a 1-4 bond.

According to one even more preferential embodiment of the invention, the compound of formula (I) is a C-glycoside derivative corresponding to formula (III):

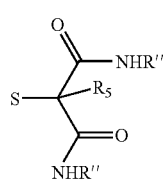

(III)

in which:
S has the meaning given above,
$R_5$ denotes:
a saturated or unsaturated, linear, cyclic or branched, unsubstituted $C_1$-$C_{12}$ alkyl group, or
a benzyl radical, or
a halogen atom, preferably a fluorine atom;
R" denotes a hydrogen atom or a saturated or unsaturated, linear, cyclic or branched $C_1$-$C_{12}$ alkyl group, optionally substituted with one or more groups chosen from —OR, —SR, —COOR, —NRR', halogen, sulphate, phosphate, glycoside, aryl and heterocycle.

The C-anomeric bond in formulae (II) and (III) may be α or β.

According to one particularly preferred embodiment of the invention, the compounds of formula (III) are such that $R_5$ is a benzyl or methyl group and R" is a methyl group.

Since the compounds of formula (III) are novel to the Applicant's knowledge, a subject of the present invention is also these novel compounds.

The invention also relates to the optical and/or geometrical isomers of the compounds of formulae (I), (II) and (III), alone or as a mixture in all proportions, and also the salts, and particularly the physiologically acceptable salts, of these compounds.

Preferred heterocycles useful herein include ring structures with e.g., 4, 5 or 6 carbon atoms, saturated or unsaturated, and further including at least one nitrogen and/or oxygen atom, more preferably piperidine, pyrimidine, pyrrolidine, and pyridine. Preferred aryl groups include phenyl, and preferred alkylcarbonyl groups comprise an alkyl chain that is saturated or unsaturated having from, e.g., 1 to 20 carbon atoms and more preferably 1, 2 or 10-12 carbon atoms.

Preferred C-anomeric bonding is such that the C—OH anomeric bond of the sugar (e.g., monosaccharide or a polysaccharide) has been replaced by a C—C bond. Preferably the C-anomeric bonding denotes the following:

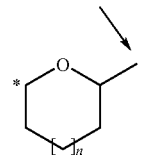

Table 1 below provides a non-limiting list of examples of compounds that may be used in the present invention. Invention compounds may be prepared, for example, according to the process described by Gonzales M. A. et al., Carbohydrate Research, 158 (1986 pp. 53-66 and by Wulff G. et al. in Carbohydrate Research 257 (1994) pp. 81-95, and also in Example 1 below with reference to the attached FIG. 1. Such preparation is within the skill of the ordinary artisan in view of the present disclosure.

TABLE 1

| Compound | Formula | R1 | R5 | R2 | m | X,Y | R'' | n |
|---|---|---|---|---|---|---|---|---|
| A | (pyranose with CH₂OH, 3 OH; C(Bn)(C(O)NHMe)₂) | benzyl | benzyl | —OH<br>—CH₂OH | 4 | —NHCH3 | —CH3 | 1 |
| B | (pyranose with CH₂OH, 3 OH; C(Bn)(C(O)NHMe)₂, different stereochem) | benzyl | benzyl | —OH<br>—CH2OH | 4 | —NHCH3 | —CH3 | 1 |
| C | (tetrahydropyran; C(Bn)(C(O)NHMe)₂) | benzyl | benzyl | — | 0 | —NHCH3 | —CH3 | 1 |
| D | (disaccharide; C(Bn)(C(O)NHMe)₂) | benzyl | benzyl | —OH<br>—CH2OH<br>-sugar | 4 | —NHCH3 | —CH3 | 1 |
| E | (pyranose with CH₂OH, 3 OH; C(Bn)(C(O)NH₂)₂) | benzyl | benzyl | —OH<br>—CH2OH | 4 | —NH2 | H | 1 |
| F | (6-deoxy pyranose; C(Bn)(C(O)NHMe)₂) | benzyl | benzyl | —OH<br>—CH3 | 4 | —NHCH3 | —CH3 | 1 |

TABLE 1-continued

| Compound | Formula | R1 | R5 | R2 | m | X,Y | R" | n |
|---|---|---|---|---|---|---|---|---|
| G | | —CH2—C6H5 | —CH2—C6H5 | —OH | 3 | —NHCH3 | —CH3 | 1 |
| H | | —CH3 | —CH3 | —OH<br>—CH2OH | 4 | —NHCH3 | —CH3 | 1 |
| I | | —CH2—CH3 | —CH2CH3 | —OH<br>—CH2OH | 4 | —NHCH3 | —CH3 | 1 |
| J | | F | F | —OH<br>—CH2OH | 4 | —NHCH3 | —CH3 | 1 |
| K | | —CH2—C6H5 | —CH2—C6H5 | —OH<br>—CH2OH | 4 | —NHCH3 | —CH3 | 1 |
| L | | H | H | —OH<br>—CH2OH | 4 | —OH | — | 1 |

The composition according to the invention preferably contains a physiologically acceptable medium and one or more compounds according to the invention in an amount that is effective to promote the desquamation of the skin, for example in an amount ranging from 0.01% to 30% by weight and preferably from 0.1% to 5% by weight relative to the total weight of the composition.

The term "physiologically acceptable medium" means a medium that is compatible with the skin and optionally with mucous membranes, the nails, the scalp and/or the hair.

The composition according to the invention may especially be in the form of an aqueous solution or a dispersion of the lotion or serum type, in the form of emulsions of liquid or semi-liquid consistency of the milk type, obtained by dispersing a fatty phase in an aqueous phase (O/W) or conversely (W/O), or in the form of suspensions or emulsions of soft consistency of the aqueous or anhydrous cream or gel type, or alternatively in the form of microcapsules or microparticles, or in the form of vesicular dispersions of ionic and/or nonionic type. These compositions can be prepared according to known methods.

This composition may be more or less fluid and may have the appearance of a white or coloured cream, an ointment, a milk, a lotion, a serum, a paste or a mousse. It may optionally be applied to the skin in the form of an aerosol. It may also be in solid form, for example in the form of a stick. It may be used as a care product, as a cleansing product, as a makeup product or as a shampoo or conditioner.

When the composition according to the invention is an emulsion, the proportion of the fatty phase can preferably range from 5% to 80% by weight and more preferably from 5% to 50% by weight relative to the total weight of the composition. The oils, waxes, emulsifiers and co-emulsifiers used in the composition in emulsion form are chosen from those conventionally used in cosmetics. The emulsifier and co-emulsifier are preferably present in the composition in a proportion ranging from 0.3% to 30% by weight and more preferably from 0.5% to 20% by weight relative to the total weight of the composition. The emulsion may also contain lipid vesicles.

As oils or waxes that may be used in the invention, mention may be made of mineral oils (liquid petroleum jelly), plant oils (liquid fraction of shea butter or sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils.

As emulsifiers that may be used in the invention, examples include glyceryl monostearate, polysorbate-60 and polyethylene glycol stearates (20 EO, 40 EO and 100 EO).

The composition of the invention may also contain adjuvants such as those that are common in cosmetics and dermatology, such as hydrophilic or lipophilic gelling agents, hydrophilic or lipophilic active agents, preserving agents, antioxidants, solvents, fragrances, fillers, screening agents, pigments, chelating agents and dyestuffs. The amounts of these various adjuvants are those conventionally used in the fields under consideration, for example from 0.01% to 20% of the total weight of the composition. Depending on their nature, these adjuvants may be introduced into the fatty phase, into the aqueous phase, into lipid vesicles and/or into nanoparticles. They will preferably be chosen so as not to harm the desquamating properties of the compounds according to the invention.

As hydrophilic gelling agents that may be used in the invention, preferred examples include carboxyvinyl polymers (Carbomer), acrylic copolymers such as acrylate/alkylacrylate copolymers, polyacrylamides, polysaccharides such as hydroxypropylcellulose, natural gums and clays, and lipophilic gelling agents that may be mentioned include modified clays, for instance bentones, metal salts of fatty acids, for instance aluminium stearates, and hydrophobic silica.

The composition according to the invention may be intended for cosmetic or pharmaceutical application, especially dermatological application. The composition according to the invention is preferably intended for cosmetic application.

A subject of the invention is thus also a cosmetic process for treating the skin or the scalp, comprising the topical application to the skin or the scalp of the composition described above.

Given the desquamating properties of the compounds according to the invention, this process is particularly intended to prevent or fade out the signs of ageing of the skin and/or to improve the radiance of the complexion and/or to combat dry skin.

A subject of the invention is thus also a cosmetic process for preventing or fading out the signs of ageing of the skin and/or for improving the radiance of the complexion and/or for combating dry skin, comprising the topical application to the skin of a composition as defined above.

A subject of the invention is also the use of the composition defined above for the manufacture of a dermatological preparation for treating acne or hyperkeratosis.

In addition, while not bound by a particular theory, the desquamating properties of the compounds according to the invention are believed to possibly be due to their ability to bind to the active site of the glycosidases involved in the desquamation process. Thus, compounds according to the invention can be used to inactivate certain epidermal glycosidases and thus provide anti-desquamating properties leading to thickening of the stratum corneum, which can be exploited for protecting the skin against UV rays and pollutants.

A subject of the present invention is thus also a cosmetic process for protecting the skin against the harmful effects of UV rays and pollution, comprising the topical application to the skin of the composition according to the invention.

Moreover, endogenous β-glycosidases are involved in the deglycosylation of lipid precursors such as glucosylceramides to ceramides, which is one of the steps in the maturation of the intercorneocytic lipids that participate in the "barrier" function of the epidermis. By stimulating the β-glycosidases, the compounds according to the invention can thus reinforce the barrier function of the skin. This property of the compounds according to the invention also makes it possible, by reducing the evaporation of the water contained in the skin, to maintain a good level of moisturization of the skin.

A subject of the present invention is thus also a cosmetic process for improving the barrier function of the skin and/or for moisturizing the skin, comprising the topical application to the skin of the composition according to the invention.

Other characteristics and advantages of the invention will emerge more clearly from the examples that follow, which are given as non-limiting demonstrations. In the text hereinbelow, the proportions are given as percentages by weight, unless otherwise mentioned.

EXAMPLES

Example 1

Preparation of 2-benzyl-N,N'-dimethyl-2-(3,4,5-trihydroxy-6-methyltetrahydropyran-2-yl)malonamide FIG. 1 illustrates a process for preparing 2-benzyl-N,N'-dimethyl-2-(3,4,5-trihydroxy-6-methyltetrahydropyran-2-yl)malonamide in three steps.

First Step

Fucose (1 g; 1 equivalent), the barbituric derivative (0.95 g; 1.5 equivalents) and 20 ml of water are placed in a round-bottomed flask. Sodium hydrogen carbonate in water is added to pH 7 and the mixture is heated at 80° C. until the starting materials have disappeared (about 5 hours).

The water is evaporated until only a minimum volume remains, so as to dissolve the residue obtained. The residue is precipitated from methanol and is then filtered off and dried under vacuum using diphosphorus pentoxide. 1.7 g of a solid product are recovered (yield: 86%). The mass spectrometry and the NMR (400 MHz) are in accordance with the expected structure.

Second Step

The compound obtained from the first step (0.2 g; 1 equivalent) and benzylbromide (0.1 ml; 1.3 equivalents) are introduced into 4 ml of DMF in a round-bottomed flask. The mixture is stirred at room temperature until the starting materials have disappeared (about 5 hours).

The solvent is evaporated off and the residue is then extracted three times with toluene, followed by three extractions with ethyl acetate. The ethyl acetate phases are dried over sodium sulphate. After evaporation, 0.15 g of an oily product is obtained (yield: 62%).

The mass spectrometry and the NMR (400 MHz) are in accordance with the expected structure.

Third Step

The compound obtained from the second step (0.1 g; 1 equivalent) is introduced into 0.5 ml of water in a round-bottomed flask. 0.5 ml (2 equivalents) of sodium hydroxide (1 M) is added and the mixture is stirred at room temperature for 30 minutes. Acetic acid is then added and the mixture is stirred for a further one hour. The reaction medium is evaporated and dried to give 0.17 g of a pasty product (yield: >100% on account of the presence of sodium acetate associated with the product). The mass spectrometry and the NMR (400 MHz) are in accordance with the expected structure.

Example 2

Demonstration of the Desquamating Effect of the Compounds According to the Invention The test consists in counting the corneocytes released after incubation of batches of isolated stratum corneum in the presence of three test compounds, corresponding to compounds F, G and K of Table 1.

Protocol:

Compounds F, G and K were each dissolved to 2% by weight in a 0.1% Triton X100 PBS buffer at pH 7.4.

Two different samples of stratum corneum isolated by trypsin/heat from plastic surgeries were used. SCI discs 4 mm in diameter were cut out using a punch and placed in the bottom of a 96-well dish. 50 µl of buffer containing the test compound were added to each well. Controls without compound were prepared. The tests were repeated three times. The incubation was performed at 37° C. with stirring for 24 hours. 10 µl were then taken up and placed in a Mallassez cell. The freed corneocytes were counted by microscope.

Results:

Table 2 below collates the results obtained.

TABLE 2

| | Average number of corneocytes released | |
|---|---|---|
| Test compound | $1^{st}$ skin sample | $2^{nd}$ skin sample |
| F | 5 | 12 |
| G | 13 | 12 |
| K | 7 | 5 |
| Control | 1 | 4 |

This test thus shows that the compounds according to the invention increase the amount of corneocytes released by the isolated stratum corneum, and can thus be used as desquamating agents.

Example 3

Anti-Ageing Fluid

| | |
|---|---|
| Compound F | 1% |
| Octyldodecanol | 5% |
| Sunflower oil | 11% |
| EDTA | 0.05% |
| Xanthan gum | 0.2% |
| Polyacrylamide/isoparaffin/laureth-7 (Sepigel 305 sold by the company SEPPIC) | 0.9% |
| Cyclopentasiloxane | 5% |
| Glycerol | 4% |
| Polyglyceryl acrylate at 2% in a water/glycerol mixture (Lubrajel sold by the company Guardian) | 5% |
| Glyceryl Stearate | 0.6% |
| Polyoxyethylene stearate (100 EO) | 0.6% |
| Polyoxyethylene stearate (20 EO) | 1.2% |
| Stearic acid | 0.6% |
| Stearyl alcohol | 1% |
| Preserving agents | 0.3% |
| Water | qs 100% |

This fluid, applied morning and evening, makes it possible to attenuate the signs of ageing of the skin and to improve the radiance of the complexion.

Example 4

Antiacne Gel

| | |
|---|---|
| Compound E | 3.0% |
| 90° ethanol | 50.0% |
| Propylene glycol | 45.5% |
| Hydroxypropylcellulose | 1.5% |

Example 5

Moisturizing Cream

| | |
|---|---|
| Compound I | 6.0% |
| Glyceryl monostearate | 0.8% |
| Cetyl alcohol | 2.0% |
| Stearyl alcohol | 5.0% |
| Polyoxyethylene stearate (20 EO) | 3.0% |
| Crosslinked acrylic acid (Carbopol 941) | 0.3% |
| Caprylic/capric triglycerides | 12.0% |
| Preserving agents | qs |
| Water | qs 100% |

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition suitable for topical application to the skin or the scalp, comprising, in a physiologically acceptable medium, at least one compound of formula (I):

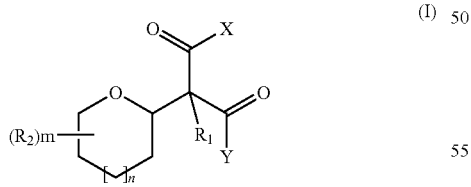

wherein $R_1$ is selected from the group consisting of, hydrogen, methyl, ethyl, fluorine, and benzyl, each $R_2$ group is independently selected from the group consisting of hydroxyl, hydroxymethyl, and methyl, X is selected from the group consisting of $NH_2$, $NHCH_3$, and OH, Y is selected from the group consisting of $NH_2$, $NHCH_3$, and OH, n is 1, and m is an integer equal to 0, 3 or 4, wherein the compound is present in an amount ranging from 0.1 to 6% by weight with respect to the total weight of the composition.

2. The composition according to claim 1, wherein the compound of formula (I) is a C-glycoside derivative corresponding to formula (II) below:

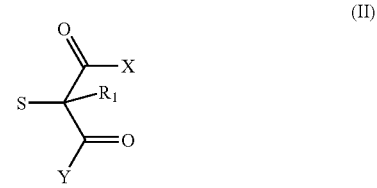

in which:

$R_1$ is selected from the group consisting of hydrogen, methyl, ethyl, fluorine, and benzyl, X is selected from the group consisting of $NH_2$, $NHCH_3$, and OH, Y is selected from the group consisting of $NH_2$, $NHCH_3$, and OH, S represents a monosaccharide, in pyranose form and of L and/or D series, the monosaccharide comprising at least one free hydroxyl function, and the S—C bond represents a bond of C-anomeric nature.

3. The composition according to claim 1, wherein the compound of formula (I) is a C-glycoside derivative corresponding to formula (III):

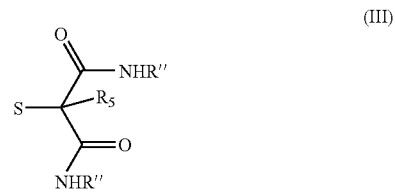

in which:

S represents a monosaccharide, in pyranose form and of L and/or D series, the monosaccharide comprising at least one free hydroxyl function, the S—C bond represents a bond of C-anomeric nature, $R_5$ is selected from, methyl, ethyl, fluorine, and benzyl, and R" denotes a hydrogen atom or a methyl group.

4. The composition according to claim 2, wherein S is a monosaccharide selected from the group consisting of D-glucose, D-galactose, D-mannose, D-xylose, D-lyxose, L-fucose and L-rhamnose.

5. The composition according to claim 3, wherein $R_5$ is a benzyl or methyl group and R" is a methyl group.

6. A cosmetic process for treating the skin or the scalp, comprising topically applying to the skin or the scalp the composition of claim 1.

7. A cosmetic process for treating the signs of ageing of the skin and/or for improving the radiance of the complexion and/or for combating dry skin, comprising topically applying to the skin the composition as defined in claim 1.

8. A cosmetic process for protecting the skin against the harmful effects of UV rays and pollution, comprising topically applying to the skin the composition as defined in claim 1.

9. Cosmetic process for improving the barrier function of the skin and/or for moisturizing the skin, comprising topically applying to the skin the composition as defined in claim 1.

10. The composition according to claim 3, wherein S is a monosaccharide selected from the group consisting of D-glucose, D-galactose, D-mannose, D-xylose, D-lyxose, L-fucose and L-rhamnose.

11. The composition according to claim 1, wherein $R_1$ is selected from the group consisting of methyl, ethyl, and benzyl, each $R_2$ group is independently selected from the group consisting of hydroxyl, hydroxymethyl, and methyl, X is selected from the group consisting of $NH_2$, $NHCH_3$, and OH, Y is selected from the group consisting of $NH_2$, $NHCH_3$, and OH, and m is an integer equal to 0, 3 or 4.

12. The composition according to claim 1, wherein $R_1$ is benzyl, each $R_2$ group is independently selected from the group consisting of hydroxymethyl, hydroxyl, and methyl, X and Y are $NHCH_3$, and m is an integer equal to 3 or 4.

13. The composition according to claim 1, wherein $R_1$ is benzyl, $R_2$ is hydroxyl, X and Y are $NHCH_3$, and m is an integer equal to 3.

14. The composition according to claim 1, comprising at least one of the following compounds:

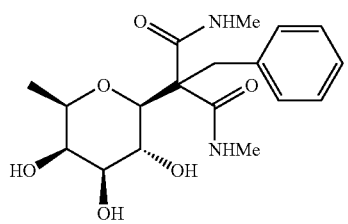

-continued

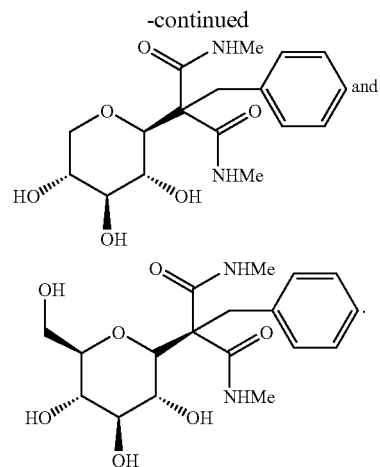

15. The composition according to claim 1, wherein the compound is present in an amount ranging from 0.1 to 5% by weight with respect to the total weight of the composition.

16. The composition according to claim 1, wherein the compound is present in an amount ranging from 1 to 6% by weight with respect to the total weight of the composition.

17. The composition according to claim 1, wherein the compound is present in an amount ranging from 3 to 6% by weight with respect to the total weight of the composition.

* * * * *